United States Patent [19]

Raviv et al.

[11] Patent Number: 4,949,725
[45] Date of Patent: Aug. 21, 1990

[54] APPARATUS AND METHOD FOR DISPLAYING ELECTRICAL ACTIVITY GENERATED WITHIN A LIVING BODY

[75] Inventors: Gil Raviv, Deerfield; Ivan Pal, Highland Park; Dean Koester, Grayslake; David Kripal, Gurnee, all of Ill.; James N. Towle, Kirkland, Wash.

[73] Assignee: Bio-Logic Systems Corporation, Mundelein, Ill.

[21] Appl. No.: 214,753

[22] Filed: Jul. 1, 1988

[51] Int. Cl.[5] .............................................. A61B 5/04
[52] U.S. Cl. .................................................. 128/731
[58] Field of Search .............................. 128/731–732, 128/699; 364/413.06, 413.07, 413.13

[56] References Cited

U.S. PATENT DOCUMENTS

| | | | |
|---|---|---|---|
| 3,816,849 | 6/1974 | Kinoshita et al. | 128/699 X |
| 4,292,977 | 10/1981 | Krause et al. | 128/712 |
| 4,416,288 | 11/1983 | Freeman | 128/731 |
| 4,478,223 | 10/1984 | Allor | 128/731 X |
| 4,649,482 | 3/1987 | Raviv et al. | |
| 4,697,597 | 10/1987 | Sanz et al. | 128/699 |
| 4,700,712 | 10/1987 | Schmid | 364/413.06 |
| 4,736,751 | 4/1988 | Gevins et al. | 128/732 |

OTHER PUBLICATIONS

Freeman, W. J., "A Software Lens for Image Reconstitution of the EEG", Prog. in Brain Research, 54: 123–127, 1981.
Wilson et al., "The Electric Field in an Electric Dipole in a Homogenious Spherical Conducting Medium", 1950.
Witwer et al., IEEE Transactions Biomedical Engineering, Sep. 1972, pp. 352–362, "The Effect of Media Inhomogeneities on Intracranial Electrical Fields".
Brody et al., IEEE Transaction Biomedical Engineering, Mar. 1973, pp. 141–143, "Electric Dipolein a Spherical Medium: Generalized Expression for Surface Potentials".
Fender, Chapter 13, "Source Localization of Brain Electrical Activity".
Scherg et al., Electroencephaly and Clinical Neurophysiology, 1985, vol. 62, pp. 32–34, "Two Bilateral Sources of the Late AEP as Identified by a Spatio-Temporal Dipole Model".
Sherg et al., Electroencephalography and Clinical Neurophysiology, 1985, vol. 62, pp. 290–299, "A New Interpretation of the Generators of BAEP Waves I–V; Results of a Spatio-Temporal Dipole Model."
Rose et al., Annals of Neurology, vol. 22, No. 3, Sep. 1987, "Location of Magnetic Iterictal Discharges in Temporal Lobe Epilepsy".

Primary Examiner—Francis Jaworski
Attorney, Agent, or Firm—Niro, Scavone, Haller & Niro, Ltd.

[57] ABSTRACT

An apparatus and method for display of biologically induced electrical activity is disclosed. The apparatus includes sensors for measuring EEG or MEG signals from a living body and using these signals to compute one or more dipoles representative of the measured electrical activity. Values of the electrical activity may also be computed for discrete locations in or on the body. The operator has the ability to input a variety of different computational specifications or criteria to facilitate dipole computation. The resulting computed data may be selectively displayed as a dipole within a three-dimensional representation of the body, as a movie-like series of dipoles, as a composite or tracing of dipoles or as various topographic maps. The operator also has the ability to change the display to provide different perspective views or to enlarge the displayed scene.

49 Claims, 6 Drawing Sheets

APPARATUS AND METHOD FOR DISPLAYING ELECTRICAL ACTIVITY GENERATED WITHIN A LIVING BODY

BACKGROUND OF THE INVENTION

The present invention relates to apparatus and methods for displaying biologically induced electrical activity. More particularly, the present invention is directed to automated, user-friendly systems for generating video displays representing the electrical activity induced by neurons in the brain.

It is known to those of skill in the art that specific combinations of sources within a living body, such as the brain, will generate at any given instant, a unique distribution of electrical potentials or magnetic fields. In the case of the brain, electrical activity generated by neurons within the brain can be measured at the surface of the scalp in the form of electric potentials or magnetic fields. These potentials or fields, in turn, can be used to determine a resultant source or current dipole, frequently called simply a "dipole".

In recent years, there has been increasing interest in the study of dipoles to assist in the diagnosis and treatment of neurological disorders. However, the methodology employed to determine the location, orientation and magnitude of any one or more dipoles at a given instant in time is mathematically complex and relatively time consuming. Moreover, known display techniques have proven less than satisfactory for the efficient and effective study of dipoles in the clinical environment. As a result, the clinical use of dipole analysis in the examination of neurological disorders is minimal, if not non-existent, at the present time.

SUMMARY OF THE INVENTION

The present invention is directed in its broadest terms to an apparatus and method for displaying electrical activity generated within a living body. In accordance with the present invention, measurements taken externally of the body by non-invasive techniques permit the determination and display of electrical activity from within the body. The electrical activity is depicted in the form of one or more dipoles or other electrical phenomena properly positioned and oriented within an image of the body. While the invention will be principally described through embodiments in which dipoles are the depicted form of electrical activity, it is intended that the invention embraces other embodiments in which other electrical phenomena are depicted, such as arrays or matrices of positive and negative charges. Thus, the invention embraces various visual representations which quantify, qualify and locate electrical activity within a living body.

The apparatus of the present invention is automated so that the mathematical computation of the dipole may be accomplished in a relatively short time period using well known algorithms developed for this purpose. Moreover, the apparatus permits the operator to view the dipole within the body from different perspectives, or as a series of dipole displays over time, or even as a tracing or composite of a plurality of dipoles over a given time period. Still further, the apparatus permits the dynamic, interactive input of the operator to employ preselected dipole criteria to facilitate computation of the dipole and its analysis upon display. The apparatus of the present invention also provides additional techniques not previously available for generating topographic maps of brain electrical activity wherein such maps are derived in whole or in part from previously computed dipoles. Moreover, the apparatus may be used to produce topographic maps resulting from the input of a given or hypothetical dipole (or dipoles). In this manner, the operator may input the necessary parameters for a given dipole and observe the resulting topographic map. By repeating this procedure with different dipoles, the operator will gain an appreciation for the relationship between dipoles and topographic maps, thereby enhancing his or her intuitive skills for topographic map interpretation.

It is therefore an object of the present invention to provide an apparatus and method for the display of brain electrical activity represented by one or more dipoles.

It is a further object of the present invention to provide an apparatus wherein dipoles may be viewed within a pictorial representation of the human head from different perspectives.

Another object of the present invention is to provide an apparatus wherein dipoles computed at successive instants in time are displayed in series or as a composite or tracing within a pictorial representation of the human head.

Still another object of the present invention is to provide an apparatus for the display of dipoles which have been computed from electrical potentials or magnetic fields measured on the surface of the scalp and wherein an operator may input data or preselected dipole criteria to facilitate or enhance the dipole computational process.

A still further object of the invention is to provide an apparatus wherein the computation and display of a plurality of dipoles over successive instants in time is facilitated by automated preselection of computational assumptions.

A further object of the present invention is to provide an apparatus for the display of brain electrical activity in the form of topographic maps wherein the displayed maps are derived in whole or in part from one or more previously computed dipoles.

These and other objects and advantages of the present invention will become more apparent to those of ordinary skill in the art from the following description of the preferred embodiments.

BRIEF DESCRIPTION OF THE DRAWINGS

In the drawings which accompany and form a part of the description of the preferred embodiments.

DETAILED DESCRIPTION OF THE PREFERRED EMBODIMENTS

Figure 1:
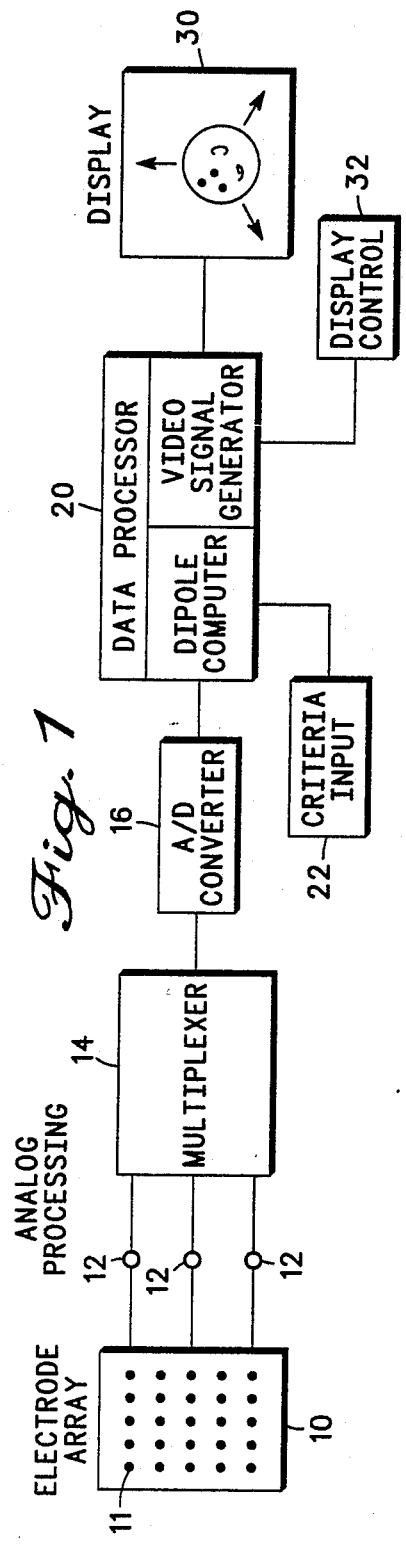
FIG. 1 is a block diagram of an apparatus according to the present invention for the display of one or more dipoles representing brain electrical activity.

With reference to FIG. 1, the apparatus of the present invention includes a sensor array 10 comprising a plurality of sensors 11 for detecting a characteristic of brain electrical activity at various spaced locations on the surface of the scalp. Typically, the detected characteristic is electrical potential used in electroencephalography (EEG) or a magnetic field used in magnetoencephalography (MEG).

While the present invention is not limited to any specific number of sensors 11, practical considerations suggest that approximately four to sixty-four sensors be used. Fewer sensors result in a less expensive apparatus which can be set up in a shorter period of time, but versatility and computed dipole accuracy are compromised. More sensors permit the utilization of more sophisticated or complex models, the calculation of more dipoles and more accurate computation, but the number of sensors is limited to the space available on the scalp and the practical constraint that more time is required to properly apply them in the desired array.

The apparatus also includes a data processor means 20 for computing the location, direction or orientation and magnitude of at least one dipole which corresponds to the sensed and measured electrical characteristic. Finally, the apparatus includes means for generating a video signal, preferably part of the data processor 20, and means for presenting a video display such as color monitor 30.

The display apparatus is designed to sample each of the sensors 11 in the array 10 to detect the preselected characteristic, i.e. electric potential (EEG signals) or magnetic field (MEG signals), at a rate sufficient to ensure that an accurate amplitude is obtained. Sampling rates may be selected by the operator from about five microseconds to about twenty milliseconds. The signal detected by each sensor 11 is then processed by an analog signal processor means 12 which typically includes a preamplifier and a band pass filter to permit only the band of signal frequencies of interest to be further processed by the apparatus. The thus processed analog signal from each sensor 11 is next input to a multiplexer 14 which acts to sequentially sample each of its plurality of inputs and to generate a multiplexed output signal. This multiplexed signal is then input to an analog to digital converter 16 which acts to generate a separate digital signal for each sensor 11. All of the foregoing apparatus is conventional in its construction and operation and a variety of alternative components suitable for generating the desired digital signals will be apparent to those skilled in the art.

Once the required digitized input data signals are obtained the data processor 20 is used to compute the dipole that corresponds to this input data. A suitable data processor might comprise any one of the various micro or mini computers now commercially available, such as one selected from the PC of PS2 families of IBM computers. There are a variety of known algorithms that may be employed for the dipole computation.

When dealing with source or dipole localization problems, in an ideal case a physical model can properly describe the full complexity of the real or actual system. This is the case, for example, in some models used to describe a radioactive source in a well known medium. In this case, the propagation of radioactive waves can be fully described in mathematical form. This means that the mathematical model fully reflects the physical model which in turn is an exact representation of the real situation. A similar case is when a dipole current source is located in a tank filled with an electrolyte of known electrical characteristics. In more complex cases, where the source or dipole is within active biological tissue and the medium is not homogeneous and is located with a body having a complicated shape, a physical model is typically employed which is not an exact representation of the real life system. This is necessary because all details of the system are not known or consideration of all details results in such a complicated model that it cannot be handled or is too expensive to handle.

Models suitable for use in the practice of the present invention only approximate the real situation but can still be very useful. Likewise, to avoid unnecessary complication or expense, a mathematical model can be chosen which only approximates the physical model.

When dealing with brain activity where several billion neurons may be active at the same time an exact physical model is practically impossible to handle even with supercomputers. There is also a significant amount of information about the system which is yet unknown. In this situation, it is useful to employ more than one model to compare their different results. Some models allow the investigator to incorporate newly obtained knowledge (e.g. conductivities in the nonhomogeneous model). Since the localization procedures are realized in software, new models can also be easily added to the system.

Any one of several models well known to those of skill in the art may be used in the practice of the present invention. The more complex the chosen model, the more time is needed for the computation. Theoretically, the more complex the chosen model, the more accurate the result of source localization. On the other hand, the accuracy of sensor or electrode measurement limits the accuracy of dipole localization. Thus, the choice of a more complicated model which in case of perfect measurement would result in more accurate dipole localization might cause extra expenses in computation time and is not always justified in the case of less accurate sensor measurements.

A model is typically constructed by making certain basic assumptions in the following categories:
1. The number of dipoles.
2. The shape and conductivity of the body in which the dipoles are located.
3. Electric currents corresponding to the activity of the dipoles are conducted through the given body by volume conduction and result in a potential distribution in the body and on its surface.

Further assumptions by the user on the dipoles and the geometry and conductivity of the surrounding media can make a model more specific and allow description of relations between dipoles and surface potentials or dipoles and potentials at any point in the surrounding media in mathematical form. Prior art models used electric field theory for this formulation and achieved satisfactory results. It is well known that 6 parameters are required to describe any one given dipole; for example, dipole location (X, Y, Z) and dipole vector (Mx, My, Mz). Thus, for n dipoles it is necessary to calculate or otherwise determine 6n parameters. It is also well known that in order to practically calculate or determine these parameters, the number of parameters should be smaller than the number of sensors used for potential or magnetic field measurement. Therefore, in the case of n dipoles, the number of sensors required would be more than 6n. A model, however, can describe a combination of n dipoles using less than 6n parameters if the dipoles are considered to be related or otherwise dependent. For example, the location of 2 independent dipoles can be described by 6 parameters, i.e. their coordinates in the 3-D space: (X1, Y1, Z1) and (X2, Y2, Z2). However, if the dipoles are assumed to be symmetric to the sagittal plane of the head, i.e. located symmetrically in the 2 hemispheres then the number of independent parameters to be estimated for dipole location is reduced to 3, because X1+X2, Z1+Z2 and Y1+ −Y2. Thus, the twelve parameters required to fully describe two dipoles can be reduced to nine parameters, or, if dipole moments symmetry is assumed, then to six parameters. More complex geometric and functional models can relate other parameters to each other, so that the number of parameters to be estimated (6n) can be decreased by one for each dipole parameter that can be described as a linear combination of other dipole parameters.

In a relatively simple model the body is approximated by an isotropic sphere with constant conductivity across space, surrounded by non-conductive medium (air). The potential at any given location on the surface of the sphere resulting from the presence of a dipole inside the sphere can be written in a mathematical formula as a function of the dipole location, dipole moment and the coordinates of the surface point. This is well known in the art and is more completely described in Brody et al, "Eccentric Dipole in a Spherical Medium: Generalized Expressions for Surface Potentials" *IEEE Transactions on Biomedical Engineering*, Vol. BME-20, 1973, pp. 141–143 and Sencaj et al, "Dipole Localization of Average and Single Visual Evoked Potentials" IEEE Transactions on Biomedical Engineering, Vol. BME-29, 1982, pp. 26–33.

The potential at a surface point E in this model is:

$$V_8 = F^*M \tag{1}$$

where $F = [F_x, F_y, F_z]$ is the lead vector and
$M = [M_x, M_y, M_z]^T$ is the dipole moment.

Figure 3:
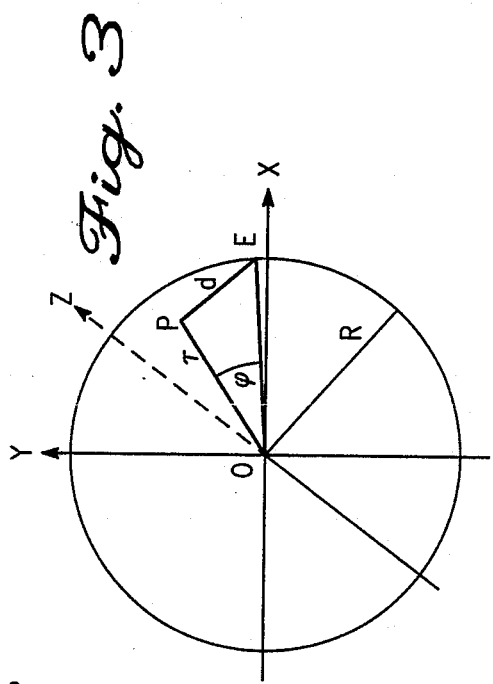
FIG. 3 is a diagram serving to illustrate certain mathematical computations associated with determination of satisfactory dipoles.

If the dipole is located at point p then the x component of the lead vector can be written as:

$$F_x = \{2(E_x - P_x)/d^2 + E_x/R^2 + [(E_x S/R - RP_x)/(d + R - S/R)]/R^2\}/4\pi Cd \tag{2}$$

where
$E_x$ and $P_x$ are the x coordinates of points $E$ and $P$ respectively, d is the Euclidean distance between E and P, R is the radius of the sphere, C is its conductivity and $$S = E_x P_x + E_y P_y + E_z P_z, \text{ or with other words} \tag{3}$$
$$S/R = r\cos\rho$$

where r is the distance of P from the origin and P is the angle between OP and OE. See FIG. 3.

Figure 4:
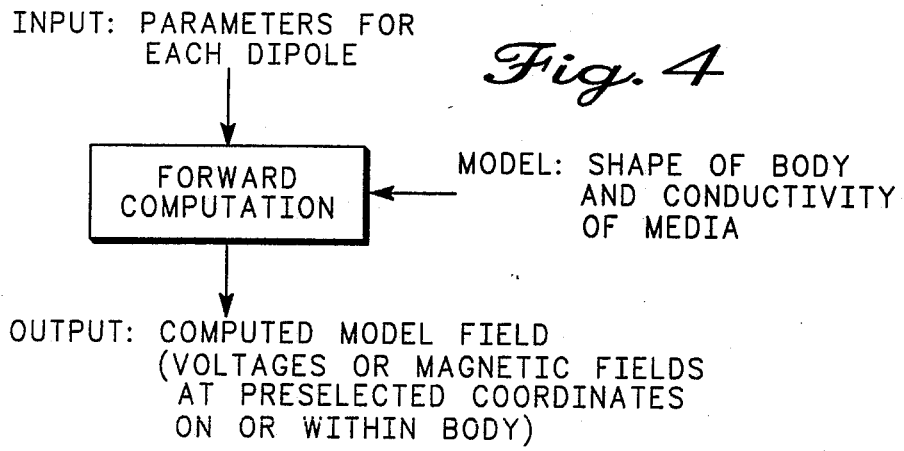
FIG. 4 is a flow chart the input and output of the data processor for the mathematical computations used in the solution of the forward problem.

Similar formulae can be written for the y and z components of F. This formulation allows the computation of surface potentials for a given dipole, i.e. the solution of the so called forward or direct problem according to equation (1). See also FIG. 4.

The computation of dipole coordinates and moments from the set of surface potentials is called the inverse problem in prior art.

The inverse problem can be solved by minimizing the difference between the measured potential field and the one which follows from the dipole solution. Thus, dipole parameters are calculated so that their resulting field or computed model values are most similar to the measure field. Several methods well known in the art can be used for this purpose, such as the optimization methods described by Eveleigh, *Control and Optimization Techniques*, McGraw-Hill, New York, 1967 or the nonlinear least squares parameter estimation described by Bevington, *Data Reduction and Error Analysis in the Physical Sciences*, McGraw-Hill, New York, 1969, pp. 204–247.

The inverse problem usually is solved by an iterative way. This can work also if an analytic solution does not exist. A set of initial values are chosen for the parameters to be estimated. In case of the above dipole model initial values are assigned to the dipole coordinates and moments:

$$P_0 + [P_{x0}, P_{y0}, P_{z0}] \text{ and } M_0 + [M_{x0}, M_{y0}, M_{z0}]$$

Figure 5:
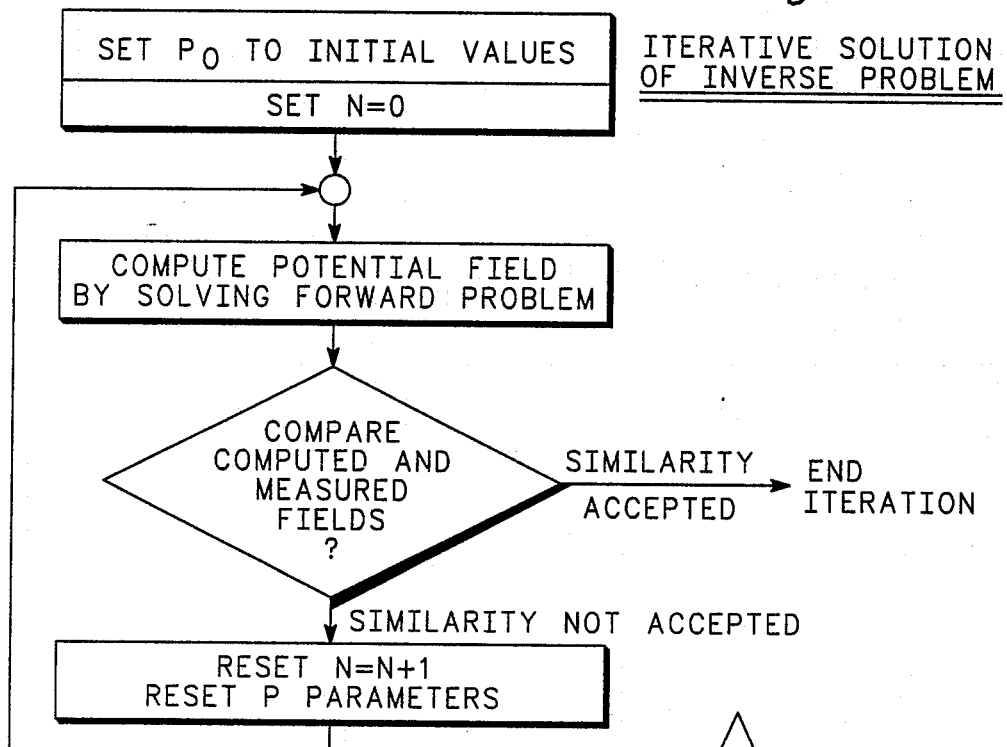
FIG. 5 is a flow chart showing certain mathematical steps in the solution of the inverse problem.

For this given dipole the forward problem is solved. The resulting potential field is compared to the measured field. If the discrepancy is larger than a preset value then the initial values are changed to a new set: P1 and M1 and a new step starts in the iteration. See FIG. 5.

There are several strategies to modify the parameters for the next iteration so that they get closer and closer to the real solution. The way to do this depends on the chosen model. In case of the above model of spherical isotropic volume a set of partial differential equations follows from the formulation of the direct problem. Partial derivatives of potentials with respect to dipole parameters can be computed this way. These partial derivatives can be used to direct the search in the parameter space.

In a somewhat more complex model the homogeneous medium with spherical boundary might be replaced by 3 concentric spheres, each being homogeneous but differing from each other in their resistivity. In case of brain potentials the three spheres might represent the brain, skull and scalp, respectively. Prior art calls these type of models 2- or 3- shell models.

The complexity of the model may be furthered by allowing the conductivity of the surrounding media to vary as a function of 3-D space. Such techniques are also well known in the art as described, for example, by Witwer et al, "The Effect of Media Inhomogeneities Upon Intracranial Electric Fields," *IEEE Transactions on Biomedical Engineering*, Vol. BME-19, 1972, pp. 352–362. In an even more general case the restriction to spherical boundary can be removed and any shape can be accepted as boundary of the conductive volume. In this model, for example, the forward problem can be formulated by the application of Kirchoff's Law as follows:

The medium is represented by a 3-D matrix of nodes. The current between 2 nodes can be given in the following finite difference form:

$$_{i,j,k}I_{i+1,j,k} = {}_{i,j,k}C_{i+1,j,k}(V_{i,j,k} - V_{i,j,k})/{}_{i,j,k}D_{i+1,j,k} \tag{4}$$

where
$_{i,j,k}I_{i+1,j,k}$ is the current between adjacent nodes $(i,j,k)$ and

-continued $(i + 1,j,k)$
$_{i,j,k}C_{i+1,j,k}$ is the conductivity between them,
$V_{i,j,k}$ is the potential at the corresponding node and,
$_{i,j,k}D_{i+1,j,k}$ is the distance between nodes $(i,j,k)$ and $(i + 1,j,k)$.
It can be shown that
$$_{i,j,k}C_{i+1,j,k} = 2/(1/C_{i,j,k} + 1/C_{i+1,j,k}) = 2/(R_{i,j,k} + R_{i+1,j,k}) \quad (5)$$
where $R_{i,j,k}$ is the resistivity at node $(i,j,k)$.
Applying Kirchoff's Law at node $i,j,k$ we get
$$B_1 V_{i+1,j,k} + B_2 V_{i-1,j,k} + B_3 V_{i,j+1,k} + B_4 V_{i,j-1,k} + \quad (6)$$
$$B_5 V_{i,j,k+1} + B_6 V_{i,j,k-1} = B_0 V_{i,j,k}$$

where $B_1 = 2/(R_{i+1,j,k} + R_{i,j,k})$
$B_2 = 2/(R_{i-1,j,k} + R_{i,j,k})$
$B_3 = 2/(R_{i,j+1,k} + R_{i,j,k})$
$B_4 = 2/(R_{i,j-1,k} + R_{i,j,k})$
$B_5 = 2/(R_{i,j,k+1} + R_{i,j,k})$
$B_6 = 2/(R_{i,j,k-1} + R_{i,j,k})$
$B_0 = B_1 + B_2 + B_3 + B_4 + B_5 + B_6$ Writing equation (6) for each node yields a set of algebraic equations. This system of equations completely describes the electric field in the given media resulting from any set of dipoles or multipoles.

Several well known techniques can be used to solve these systems of finite difference equations in order to compute the potential at any given point in the 3-D space. See for example, the iterative methods disclosed by Young, "Iterative Methods for Solving Partial Difference Equations of Elliptic Type", Transactions of the American Mathematical Society, Vol. 76, 1954, pp. 107–111; or Forsythe et al, *Finite Difference Methods and Partial Differential Equations,* Wiley, New York, 1960.

For an iterative algorithm to solve the forward problem, we can rewrite (6) for example, in the following form:

$$_{n+1}V_{i,j,k} = (1 - p)(_nV_{i,j,k}) + (p/B_0)[B_1(_nV_{i+1,j,k}) + \quad (7)$$
$$B_2(_nV_{i-1,j,k}) + B_3(_nV_{i,j+1,k}) + B_4(_nV_{i,j-1,k}) +$$
$$B_5(_nV_{i,j,k+1}) + B_6(_nV_{i,j,k-1})]$$

where subscript n denotes the value after step n of the iteration and p is the overrelaxation parameter.

The overrelaxation parameter can be chosen as a constant between 1 and 2. An alternative method to reach faster and smoother convergence is to determine an optimal value for this parameter. This can be done an iterative way, too, i.e. by recalculating an optimal value after each step, or at least after several steps in the iteration. One way to compute this parameter as suggested by Carre, "The Determination of the Optimum Acceleration Factor For Successive Overrelaxation" *Computer Journal,* Vol. 4, 1961, pp. 73–78:

$$p_{n+1} = 2/[1 + (1 - q_n)^{\frac{1}{2}}] \quad (8)$$
$$q_n = (s_n + p_n - 1)^2/s_n p_n^2$$
$$s_n = r_n/r_{n-1}$$

where subscripts denote the steps of iteration, p is the overrelaxation parameter, and r is the highest residual in the corresponding iteration.

An alternative method is the one suggested by Witwer (1972) where $P_{n+1}$ is replaced by $P'_{n+1}$ the following way:

$$(9) \quad P'_{n+1} + P_{n+1} - (2 - P_{n+1})/4$$

using these computational techniques, the forward or direct problem may be solved; that is, one or more dipoles may be defined by the various parameters described above. Having solved the direct problem, the inverse or field computation may then be solved. These complimentary solutions are made in the practice of the present invention by the following iterative computation. First, an initial solution comprising location, orientation and magnitude data is selected and input to the algorithm. This can be done by the operator or automatically. Predetermined initial solution data considered most likely to assure rapid and accurate dipole computation for a particular neurological examination may be maintained in a library stored in either internal or external memory. The data processor then computes a model field using the above-noted algorithm and compares that with the measured field. The algorithm then automatically modifies the initial solution and repeats the computation, in an iterative process, until either an acceptable solution is obtained or the data processor terminates the calculation because preselected conditions have occurred which indicate no satisfactory solution is available, given the basic assumptions and initial solution.

In order to facilitate dipole computation and permit more rapid determination of satisfactory computed dipoles, the operator may input to the data processor 20 various computing specifications or dipole criteria. This is accomplished through the criteria input means 22 which will typically include a conventional data entry keyboard. There are certain dipole criteria that have been found particularly effective in reducing computation time, such as: restricted dipole location, dipole convergence level and dipole field comparison.

Restricted dipole location restricts dipole computation to a specific zone or region. For example, the operator can input a three-point coordinate and a radius which defines the location and size of a sphere within the body being studied. If the solution obtained at any point in the iterative dipole computation is outside this defined spherical region then the computation terminates and a new initial solution or other model assumptions must be input to the data processor. Of course, regions other than spheres may be defined, or any one of a library of predetermined regions previously found of interest for a particular neurological analysis may be selected by the operator from computer memory.

Dipole convergence level restricts dipole computation to a preselected differential in dipole location. Thus, if at any time during the iterative dipole computation the difference in dipole location from one computation to the next falls below the preselected value input by the operator then the computation terminates. The thus obtained dipole may then be used by the operator, or the operator may opt to begin the iterative process again. Convergence level criteria may be entered by the operator via input means 22 or selected from a library of such criteria stored in computer memory.

Dipole field comparison restricts dipole computation to a preselected differential between the computed dipole field and the measured field. Thus, when the difference in computed and measured fields falls below a value selected and input by the operator, the dipole computation ends.

Still other dipole criteria may be useful. For example, when computing multiple dipoles it is desireable to limit the number of independent parameters to be calculated in order to reduce computation time. In such instances, the criteria entered via input means 22 may be a preselected linear or non-linear relationship between the dipoles. Examples of linear relationships include dipoles that have the same locations or locations which are positioned symmetrically within the body, or dipoles having the same direction or magnitude, or where the dipoles all have a direction normal to a given line. Once again, in each instance the operator can choose and input to data processor 20 the specific dipole criteria considered most appropriate for a given neurological examination, and in this way the operator can dynamically interact with the apparatus during the investigation.

There is one particularly useful dipole criteria for use when computing a series of dipoles from data measured at successive instants over a given period of time. In this situation, the operator may designate and input to the data processor the first satisfactorily computed dipole from one such instant in time as the initial solution for the dipole computation of the next instant in time, and so forth. In many cases, particularly where the time interval between successive instants is relatively short, i.e. one millisecond, this "progressive" dipole criteria substantially shortens computation time.

Another dipole criteria which is adapted for use with MEG signals is one which establishes a best-estimate for use as the initial solution in the iterative dipole computation. According to this dipole criteria the dipole location used in the initial solution is either automatically or manually input to the data processor 20 as a function of the distance between the maximum MEG signals measured on the scalp; namely as the point within the brain located directly below the centroid of these maximum MEG signals at a depth equal to the square root of the distance between the signals. Thus, having determined the maximum MEG signals, the dipole location of the initial solution is automatically set for use in the algorithm computation.

Having computed a satisfactory dipole the data processor 20 then uses the above-identified or other suitable algorithm to compute model field values of the electrical characteristic, either potentials or magnetic fields, at different discrete locations on or in the body. For example, the operator may select the scalp surface or a surface of particular brain lobe, and obtain computed field values for that surface. Alternatively, different planar sections of the brain can be designated for computation of field values lying in that planar section. These computed field values need not be determined for too great a number of locations, because a relatively few computed values may be expanded by well known interpolation techniques into a complete array of data for a given surface or planar section. As a result, and in accordance with one embodiment of the invention, a relatively few sensors, less than eight for example, may be used to generate a computed model field and thereafter to generate a topographic map through the use of interpolation. This will permit display of topographic maps using the apparatus of the present invention with standard evoked potential equipment that typically only uses one to eight sensors.

In accordance with another preferred embodiment of the invention, the dipole computation is carried out using fewer than all of the measured values from every sensor 11. Once a satisfactory computed dipole is obtained, given the particular algorithm and model assumptions, the solution may be tested against the remainder of the measured values. Thus, by using fewer than all of the measured values and then using the remaining values as a quality control, the system becomes self-verifying and insures that the mathematically correct solution that satisfies the algorithm is also in conformance with the real physiology involved.

In addition to these various dipole and model field computations, data processor 20 is also capable of performing other mathematical comparisons or manipulations between computed and measured field values. For example, differences, percentages or statistical comparisons can be calculated for each discrete sensor location, and the product of these mathematical comparisons may likewise be displayed as a topographic map.

Figure 2:
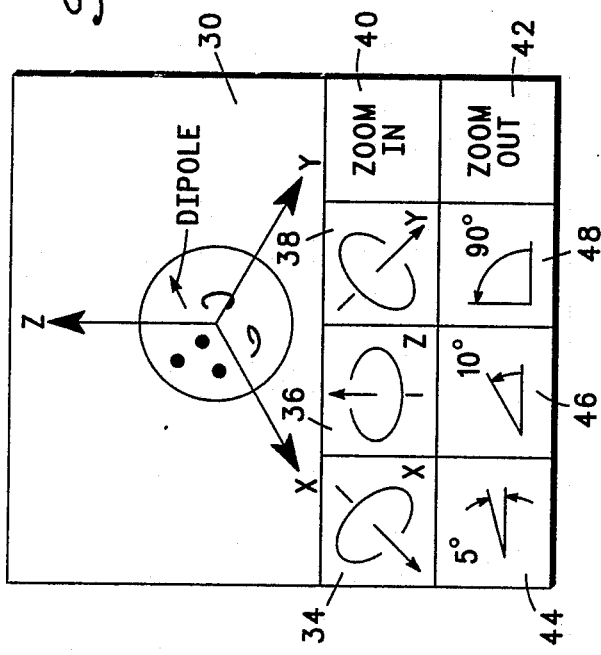
FIG. 2 is an illustration of a typical dipole display together with exemplary controls useful in changing the dipole display.

Once an acceptable solution or satisfactory dipole is obtained, the computed dipole data is either stored in memory or input to the video signal generator and ultimately transmitted to display 30. By use of the display control 32 the operator selects a particular display mode. For example, the operator may choose a dipole display which shows the dipole itself within a three-dimensional representation of the body, i.e., a human head. The display may also include reference axes to properly orient the operator to the particular perspective being displayed. A typical dipole display of this type is depicted in FIG. 2. Alternatively, the operator may select a topographic display which shows an array of computed field values in a two-dimensional representation of the head. As discussed in greater detail below, the topographic display may show computed values at the surface of the scalp or at internal locations including various cross-sections of the brain.

In accordance with one embodiment of the invention the display can be changed to provide the operator with different perspective views of the dipole display. This feature greatly enhances the operator's ability to assimilate and comprehend the information represented by the dipole. Once again, in the dipole display the viewed scene includes the three-dimensional representation of the head, the dipole and reference axes x, y, z as shown in FIG. 2. The operator may change the viewpoint by rotating the displayed scene around any of the reference axes. This is accomplished simply by actuation of the display control which may include a keyboard, a remote cursor control device or simply a series of switches. In addition, the operator may change the displayed scene by varying the apparent distance from the viewpoint to the displayed scene; that is, a closer viewpoint will provide an enlarged display while a more distant viewpoint will result in a wider range of display. With reference to FIG. 2, for example, the operator may simply actuate one of the rotational switches, 34, 36 or 38, to change the viewing perspective. Likewise, actuation of zoom-in or zoom-out switches 40 and 42, respectively, will change the apparent viewing distance. Other controls, such as increment adjustment switches 44, 46 and 48, can be used to give the operator greater flexibility. For example, actuation of switch 44 will permit axis rotation at 5° increments whereas switch 46 will allow 10° incremental rotation, and so on.

In another preferred embodiment of the invention, a series of dipoles are computed with each representing brain electrical activity at a particular instant in a selected time period. This series of computed dipoles is then displayed in series within a three-dimensional representation of the head to provide a movie-like display of brain electrical activity for the given time period. Moreover, the sequence can be repeated with the operator changing the perspective view and/or viewing distances, as described above, thereby facilitating a complete understanding of the movie-like dipole display.

The operator also has the option of selecting a composite or tracing display such that each of the series of dipoles is merged to form a continuous ribbon-like image on the display. Alternatively, each one of a series of dipoles may be displayed simultaneously, thereby permitting the operator an opportunity to visually compare one dipole with any other in the displayed series.

As noted previously, the apparatus and methods of the present invention also permit a unique approach to the generation and display of topographic maps using the dipole computation methodology. Once a satisfactory computed dipole (or dipoles) has been obtained, the data processor 20, using the above-identified algorithm can generate computed model field values for the measured electrical characteristic at discrete locations anywhere on or in the body. Thus, the operator may define a surface or an internal plane of the body, input this defined surface or plane through controller 22, and obtain the computed field values at discrete locations on the surface or plane. These computed values may be displayed alone or in combination with additional interpolated values as a topographic map. In this way, electrical activity characteristics may be displayed for locations on or in the body where no actual measurements have been obtained by sensors 11. In addition, the operator may display a plurality of topographic maps simultaneously. For example, the computed field values may be displayed in one topographic map while the measured field values are displayed on a second topographic map.

In still another preferred embodiment of the invention, the operator simply inputs a complete set of parameters defining one or more dipoles into data processor 20 and enters an instruction to generate a topographic map. The given or defined dipole data is used by processor 20 to compute a model field which is then displayed. In this way, and by inputting different dipole parameter data, the operator can gain an appreciation for the relationship between different dipoles and their respective topographic maps.

The particular electrical components, circuitry and software required t implement the apparatus and methods of the present invention are all readily available and well known to those of ordinary skill in the art. For example, U.S. Pat. Nos. 4,417,591; 4,416,288; and 4,649,482 all disclose various apparatus useful in obtaining the necessary analog and digital signals representative of measured brain electrical activity. Moreover, U.S. Pat. Nos. 4,417,591 and 4,649,482 also disclose apparatus for generation of video signals and presentation of displays suitable for use in the present invention. The disclosures of U.S. Pat. No. 4,417,591 to Culver, U.S. Pat. No. 4,416,288 to Freeman, and U.S. Pat. No. 4,649,482 to Raviv et al are all incorporated herein by reference. Likewise graphics display hardware and software packages satisfactory for use in the present invention to permit display changes in terms of perspectives or distances are now available from a variety of manufacturers. One such suitable hardware and software package is available under the tradename PG-640 Professional Graphics Board from Matrox Electronic Systems Ltd., Dorval, Quebec Canada H9B204. Another hardware package suitable for use in the present invention is available under the tradename Megagraph Enhanced Graphics Adaptor from Atronics International Inc., Milpitas Calif. 95035. This hardware may be used satisfactorily with a software package called Meta Window from Metagraphics Software Corp., Scotts Valley, Calif. 95066.

The system of the present invention provides as several possibilities to visualize the body (e.g. the head and/or brain) and the location and activity of dipoles in a 3-dimensional space. Since the computer eventually draws the picture onto a 2 dimensional screen, various (software) techniques are utilized by the system to help the operator perceive a 3-dimensional picture. The operator has control over the available algorithms in the system and can choose the most suitable representation of the body.

This can be done in case of a head for instance either by choosing a preset representation of the head or entering 3D coordinates measured on the actual patient. These coordinates can be based on measurements from stereotaxic equipment, CT scans or magnetic resonance images.

The body can be represented in the computer, for instance, by a set of characteristic lines (nonparametric curves based on actual measurements or higher order polynomials or splines can be used) or by surfaces. Curved surfaces can be approximated by parametric surfaces (e.g. cubic or bicubic surfaces) or B-spline forms. It is also possible to represent them by a set of polygons (polygon mesh representations).

Once the 3D representation is chosen, 3D to 2D transformations follow. The 3D coordinates are projected to a viewing plane. Perspective projection can be used to enhance stereo view. In some cases where exact measurements are necessary on the resulting display or a series of planar sections are to be viewed, parallel projection is a more appropriate methodology. In other cases orthographic projections can be used.

To enable the user to more easily comprehend the dipoles as they appear in the 3D representation of the body, it is possible to rotate and translate the body in 3D space, to change the viewer's distance from the object and to change the viewing angle or perspective. These adjustments can be accomplished by simple matrix operations in the software. The operator defines the origin of the 3D space where the modelling is done and the place of the viewer in this space. Rotation of the object with angle alpha around x, y or z axis can be realized through a rotation matrices (Rx, Ry, Rz) that multiply the coordinate vectors.

$$R_x = \begin{bmatrix} 1 & 0 & 0 & 0 \\ 0 & \cos(alpha) & \sin(alpha) & 0 \\ 0 & -\sin(alpha) & \cos(alpha) & 0 \\ 0 & 0 & 0 & 1 \end{bmatrix}$$

$$R_y = \begin{bmatrix} \cos(alpha) & 0 & -\sin(alpha) & 0 \\ 0 & 1 & 0 & 0 \\ \sin(alpha) & 0 & \cos(alpha) & 0 \\ 0 & 0 & 0 & 1 \end{bmatrix}$$

$$R_z = \begin{bmatrix} \cos(alpha) & \sin(alpha) & 0 & 0 \\ -\sin(alpha) & \cos(alpha) & 0 & 0 \\ 0 & 0 & 1 & 0 \\ 0 & 0 & 0 & 1 \end{bmatrix}$$

To further enhance depth perception the operator can remove or clip parts of the 3D space. It is possible to view the object as if it was transparent or to remove hidden lines, hidden edges or hidden surfaces from the picture. Several well known algorithms are available to those of ordinary skill in the art for these operations. The user must simply select the most appropriate algorithm according to the particular application. In case of viewing only a limited number of displays a slower but more precise algorithm can be used, in case of viewing a series of displays in rapid succession a faster algorithm is needed. The choice may also depend on the shape and way of representation of the 3D body. For instance, in case of mostly convex surfaces represented by a polygon mesh the norm of each polygon can be computed. If the norm is oriented towards the viewer then the polygon is drawn, otherwise it is removed from the picture.

Further improvement in 3D perception can be made by using shadows on and around the object. The operator can choose diffused or direct light and in case of the latter the angle of illumination can also be chosen.

Another possibility to help depth perception is to represent depth by different colors. In other words, one can use a color space for drawing the object, where the 3D space is built from cubes of different colors.

Stereopsis can also be chosen for enhancing 3D representation. For example, the system draws two displays of the same object on the same screen, one in red and the other in green. For the two displays the object is viewed from slightly different angles (corresponding to the eyes of the viewer). If the viewer uses special glasses (one eye looks through red the other through green) a perfect 3D illusion is presented.

Image transformations are used in the system in order to spare computation time to be able to display each new view as quickly as possible. This is of value when displaying a sequence of views of the same dipoles in rapid succession or to rotate the object into proper orientation fast.

Figure 6:
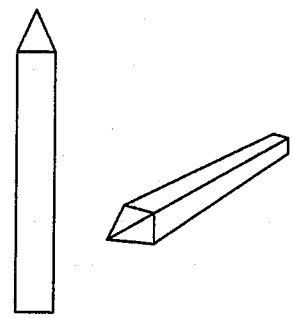
FIG. 6 is an illustration of one preferred image used to display dipoles in accordance with the present invention.

In accordance with another embodiment of the invention, the dipole or dipoles are displayed as an obelisk-like image as shown in FIG. 6. Use of such an image facilitates the operator's comprehension of the orientation of the dipole, since the pointed end depicts direction and the three-dimensional quality of the obelisk helps to properly understand the orientation of the dipole, as well.

Of course, it should be understood that various changes and modifications to the preferred embodiments described herein will be apparent to those skilled in the art. For example, while the invention has been described for use with one or more dipoles, it will find advantageous applications when used in analysis of dipole layers or multipoles. Moreover, the invention is not limited to a particular video display; both black and white and color monitors may be employed, and their respective utilities will be recognized by those in the art. Likewise, while certain dipole criteria have been disclosed, many others may be employed. Indeed, one of the advantages of the present invention is that the operator may dynamically define whatever criteria considered appropriate for the particular neurological examination. All such changes and modifications can be made without departing from the spirit and scope of the present invention and without diminishing its attendant advantages. It is, therefore, intended that such changes and modifications be covered by the following claims.

What is claimed is:

1. An apparatus for displaying electrical activity generated within a living body comprising:
 a plurality of sensors for sensing a characteristic of said electrical activity at spaced locations on the surface of said body;
 means for computing first dipole data representing one or more of the location, direction and magnitude parameters of at least one dipole disposed within said body corresponding to said sensed electrical activity characteristic;
 means for receiving and storing second dipole data representing assumed values for one or more of the location, direction and magnitude parameters of said at least one dipole;
 video display means for generating and presenting from said first dipole data or from said first and second dipole data a video display showing the location, direction and magnitude of said at least one dipole within a three dimensional representation of said body; and
 said video display means being adapted to generate further video displays to present different perspective views of said at least one dipole and said three dimensional representation of said body.

2. The display apparatus of claim 1 wherein said video display means is further adapted to depict rotation of said three dimensional representation of said body and the location, direction and magnitude of said at least one dipole about at least one of the three axes of said three dimensional representation of said body.

3. The display apparatus of claim 1 further including means for operator input of dipole criteria to facilitate said first dipole data computation.

4. The display apparatus of claim 3 wherein said operator input means is adapted to restrict the computation of first dipole data representing location to a predetermined region of said body.

5. The display apparatus of claim 3 wherein said computing means is adapted to compute a sequence of first dipole data and said operator input means includes means to compare successive first dipole data computations and to terminate first dipole data computation when the difference between said successive computations falls below a predetermined value.

6. The display apparatus of claim 3 wherein said computing means is adapted to compute a sequence of model dipole generated fields and said operator input means includes means to compare successive model dipole generated fields with the sensed electrical activity characteristic and to terminate first dipole data computation when the difference between any one model dipole generated field and the sensed electrical activity characteristic falls below a predetermined value.

7. The display apparatus of claim 1 wherein said living body is a human head and said characteristic is electrical potential.

8. The display apparatus of claim 1 wherein said living body is a human head and said characteristic is an electromagnetic field.

9. An apparatus for displaying electrical activity generated within a living body comprising:
 a plurality of sensors for sensing a characteristic of said electrical activity at spaced locations on the surface of said body;
 means for computing first dipole data representing one or more of the location, direction and magnitude parameters of a plurality of dipoles disposed within said body corresponding to said sensed electrical activity characteristic;

means for receiving and storing second dipole data representing assumed values for one or more of the location, direction and magnitude parameters of said plurality of dipoles;

means for inputting preselected dipole criteria to said computing means to facilitate first dipole data computation, said dipole criteria comprising a relationship between any of said location, direction or magnitude parameters of any one or more of said plurality of dipoles;

video display means for generating and presenting from said first dipole data or from said first and second dipole data a video display showing the location, direction and magnitude of said plurality of dipoles within a three dimensional representation of said body; and said video display means being adapted to generate further video displays to present different perspective views of said plurality of dipoles and said three dimensional representation of said body.

10. The display apparatus of claim 9 wherein said relationship is that said dipole locations are all symmetrically positioned about a central vertical plane through said body.

11. The display apparatus of claim 10 wherein said relationship is a non-linear mathematical relationship.

12. The display apparatus of claim 9 wherein said relationship is that said dipole directions are all the same.

13. The display apparatus of claim 9 wherein said relationship is that said dipole directions are all normal to a given plane or line within said body.

14. The display apparatus of claim 9 wherein said relationship is that said dipole magnitudes are all the same.

15. The display apparatus of claim 9 wherein said relationship is a linear mathematical relationship.

16. An apparatus for displaying electrical activity generated within a living body comprising:
a plurality of sensors for sensing a characteristic of said electrical activity at spaced locations on the surface of said body over a period of time;

means for computing first dipole data representing one or more of the location, direction and magnitude parameters of a sequence of dipoles disposed within said body and each corresponding to said sensed electrical activity characteristic at successive instants in time during said period;

means for receiving and storing second dipole data representing assumed values for one or more of the location, direction and magnitude parameters of said sequence of dipoles; and video display means for generating and presenting from said first dipole data or from said first and second dipole data a series of video displays, each successive video display showing the location, direction and magnitude of one of said sequence of dipoles within a three dimensional representation of said body.

17. The display apparatus of claim 16 wherein said series of video displays is displayed at a rate of at least five frames per second.

18. The display apparatus of claim 16 wherein the dipole location, magnitude and direction of each video display remains visible during all successive video displays of said series.

19. An apparatus for displaying electrical activity generated within a living body comprising;
a plurality of sensors for sensing a characteristic of said electrical activity at spaced locations on the surface of said body over a period of time;

means for computing first dipole data representing one or more of the location, direction and magnitude parameters of a series of dipoles disposed within said body and each corresponding to said sensed electrical activity characteristic at successive instants in time during said period;

means for receiving and storing second dipole data representing assumed values for one or more of the location, direction and magnitude parameters of said series of dipoles;

means for inputting preselected dipole criteria to said computing means for first dipole data computation of one of said series of dipoles at one of said instants in time, and said input means including means for inputting earlier computed first dipole data to provide the dipole criteria for a later first dipole data computation; and means for generating and presenting from said first dipole data or from said first and second dipole data a video display showing the location, direction and magnitude of said series of dipoles within a three dimensional representation of said body.

20. An apparatus for displaying electrical activity generated within a living body comprising:
a plurality of sensors for sensing a characteristic of said electrical activity at spaced locations on the surface of said body over a period of time;

means for computing first dipole data representing one or more of the location, direction and magnitude parameters of a series of dipoles disposed within said body and each corresponding to said sensed electrical activity characteristic at successive instants in time during said period;

means for receiving and storing second dipole data representing assumed values for one or more of the location, direction and magnitude parameters of said series of dipoles; and video display means for generating and presenting from said first dipole data or from said first and second dipole data a video display showing a composite defined by said series of dipoles within a three dimensional representation of said body.

21. An apparatus for displaying electrical activity generated within a living body comprising:
a plurality of sensors for sensing a characteristic of said electrical activity at spaced locations on the surface of said body;

means for generating electrical activity signals responsive to said sensed electrical activity characteristic;

means for selecting a portion of said electrical activity signals, thereby leaving a remainder of signals;

first means for computing first dipole data representing one or more of the location, direction and magnitude parameters of at least one dipole disposed within said body corresponding to said sensed electrical activity characteristic represented by said portion of electrical activity signals;

means for receiving and storing second dipole data representing assumed values for one or more of the location, direction and magnitude parameters of said at least one dipole;

second means for computing from said computed first dipole data or from said first and second dipole data model values of said electrical activity characteristic for a plurality of discrete locations on said body; and video display means for generating and presenting a video display showing the location, direction and magnitude of said at least one dipole or said computed model values of said electrical activity characteristic in association with a three dimensional representation of said body.

22. The display apparatus of claim 21 further including means for comparing said computed model values of said electrical activity characteristic with said remainder of signals to thereby verify the accuracy of said first dipole data computation.

23. The apparatus of claim 21 wherein said video display shows both computed model values and sensed values of said electrical activity characteristic.

24. The apparatus of claim 21 further including means for mathematically comparing said computed values of said electrical activity characteristic with sensed values of said electrical activity characteristic, and wherein said video display means is further adapted to present the product of said mathematical comparison as a topographic map.

25. An apparatus for displaying electrical activity generated within a living body comprising:

a plurality of sensors for sensing a characteristic of said electrical activity at spaced locations on the surface of said body;

first means for computing first dipole data representing one or more of the location, direction and magnitude parameters of at least one dipole disposed within said body corresponding to said sensed electrical activity characteristic;

means for receiving and storing second dipole data representing assumed values for one or more of the location, direction and magnitude parameters of said at least one dipole;

second means for computing from said first dipole data or from said first and second dipole data a model value of said electrical activity characteristic for each of a plurality of discrete locations on said body; and video display means for generating and presenting a video display showing said computed model value of said electrical activity characteristic at each of said discrete locations within one of either a two-dimensional or a three-dimensional representation of said body.

26. The display apparatus of claim 25 wherein said plurality of discrete locations all lie on said surface of said body.

27. The display apparatus of claim 25 wherein said plurality of discrete locations all lie on a curved plane located within said body.

28. The display apparatus of claim 25 wherein said plurality of discrete locations all lie on a cross-sectional plane of said body.

29. The display apparatus of claim 25 wherein said video display shows the computed model values of electrical activity characteristic at said discrete locations and additional interpolated values of electrical activity characteristic at locations between said discrete locations.

30. The display apparatus of claim 25 wherein the number of sensors is eight or less.

31. The display apparatus of claim 30 wherein said video display shows the computed model values of electrical activity characteristic at said discrete locations and additional interpolated values of electrical activity characteristic at locations between said discrete locations.

32. The display apparatus as defined in claim 1, 9, 16, 19, 20, or 21 further including means for coloring said display whereby different colors indicate different depths and said three dimensional representation of said body is enhanced to provide improved depth perception.

33. The display apparatus as defined in claim 32 wherein said different colors comprise varying intensity levels for one color.

34. The display apparatus as defined in claim 1, 9, 16, 19, 20, or 21 further including means for removing portions of said display to improve depth perception whereby the three dimensional representation of said body is enhanced.

35. The display apparatus as defined in claim 1, 9, 16, 19, 20, 21 or 25 further including means for shading portions of said display to improve depth perception whereby the three dimensional representation of said body is enhanced.

36. The display apparatus as defined in claim 35 further including means for inputting viewpoint, body orientation and illumination source data to said display means.

37. The display apparatus as defined in claim 1, 9, 16, 19, 20, or 21 further including means for generating said display in a stereopsis viewing format.

38. The display apparatus as defined in claim 1, 9, 16, 19, 20, or 21 further including means for inputting to said computing means actual dimensional measurements of said body such that said three dimensional representation in said display corresponds in size and shape to said body.

39. An apparatus for displaying a topographic map of computed model values of brain electrical activity comprising:

means for receiving dipole data representing the location, direction and magnitude parameters that define at least one dipole;

means for computing from said dipole data model values of brain electrical activity for a plurality of locations; and means for displaying said computed model values of brain electrical activity as a topographic map.

40. A method for display electrical activity generated within a living body comprising:

sensing a characteristic of said electrical activity at spaced locations on the surface of said body;

computing first dipole data representing one or more of the location, direction and magnitude parameters of at least one dipole disposed within said body corresponding to said sensed electrical activity characteristic;

storing second dipole data representing assumed values for one or more of the location, direction and magnitude parameters of said at least one dipole;

generating and presenting from said first dipole data or from said first and second dipole data a video display showing the location, direction and magnitude of said at least one dipole; within a three dimensional representation of said body; and changing said display to depict rotation of said three dimensional representation of said body and said at least one dipole about at least one of the three axes of said three dimensional representation of said body; to thereby provide different perspective views of said dipole within said body.

41. A method for displaying electrical activity generated within a living body comprising:
   sensing a characteristic of said electrical activity at spaced locations on the surface of said body over a period of time;
   computing first dipole data representing one or more of the location, direction and magnitude parameters of a sequence of dipoles, disposed within said body and each corresponding to said sensed electrical activity characteristic at one of successive instants in time during said period;
   storing second dipole data representing assumed values for one or more of the location, direction and magnitude parameters of said sequence of dipoles; and
   generating and presenting from said first dipole data or from said first and second dipole data a series of video displays each showing the location, direction and magnitude of one of said sequence of dipoles within a three dimensional representation of said body.

42. A method for displaying electrical activity generating within a living body comprising:
   sensing a characteristic of said electrical activity at spaced locations on the surface of said body over a period of time;
   computing first dipole data representing one or more of the location, direction and magnitude parameters of a sequence of dipoles disposed within said body and each corresponding to said sensed electrical activity characteristic at one of successive instants in time during said period;
   storing second dipole data representing assumed values for one or more of the location, direction and magnitude parameters of said sequence of dipoles; and
   generating and presenting from said first dipole data or from said first and second dipole data a video display showing a tracing defined by said sequence of dipoles within a three dimensional representation of said body.

43. A method for displaying electrical activity generating within a living body comprising:
   sensing a characteristic of said electrical activity at spaced locations on the surface of said body;
   computing first dipole data representing one or more of the location, direction and magnitude parameters of at least one dipole within said body corresponding to said sensed electrical activity characteristic;
   storing second dipole data representing assumed values for one or more of the location, direction and magnitude parameters of said at least one dipole;
   computing from said computed first dipole data or from said first and second dipole data a model value of said electrical activity characteristic for each of a plurality of discrete locations on said body; and
   generating and presenting a video display showing said computed model value of said electrical activity characteristic at each of said discrete locations without one of either a two-dimensional or a three-dimensional representation of said body.

44. A method for displaying electrical activity generated within a living body comprising:
   sensing a characteristic of said electrical activity at spaced locations on the surface of said body;
   computing first dipole data representing one or more of the location, direction and magnitude parameters of a plurality of dipoles disposed within said body corresponding to said sensed electrical activity characteristic;
   inputting preselected dipole criteria to facilitate first dipole data computation, said dipole criteria comprising a relationship between said location, direction or magnitude parameters of said plurality of dipoles;
   storing second dipole data representing assumed values for one or more of the location, direction and magnitude parameters of said plurality of dipoles;
   generating and presenting from said first dipole data or from said first and second dipole data a video display showing the location, direction and magnitude of said plurality of dipoles within a three dimensional representation of said body; and
   means for changing said display to provide different perspective views of said dipoles within said three dimensional representation of said body.

45. A method for displaying electrical activity generated within a living body comprising:
   sensing a characteristic of said electrical activity at spaced locations on the surface of said body over a period of time;
   computing first dipole data representing one or more of the location, direction and magnitude parameters of a series of dipoles within said body and each corresponding to said sensed electrical activity characteristic at one of successive instants in time during said period;
   inputting preselected dipole criteria for dipole data computation, and inputting an earlier computed dipole as the dipole criteria for a later dipole data computation;
   storing second dipole data representing assumed values for one or more of the location, direction and magnitude parameters of said at least one dipole; and
   generating and presenting a video display from said first dipole data or from said first and second dipole data showing said series of dipoles within a three dimensional representation of said body.

46. A method for displaying electrical activity generated within a living body comprising:
   sensing a characteristic of said electrical activity at spaced sensor locations on the surface of said body;
   generating electrical activity signals responsive to said characteristic for each said sensor location;
   selecting a portion of said electrical activity signals, thereby leaving a remainder of signals;
   computing first dipole data representing one or more of the location, direction and magnitude parameters of at least one dipole disposed within said body corresponding to said sensed electrical activity characteristic represented by said portion of electrical activity signals;
   computing from said computed dipole data a model value of said electrical activity characteristic for each of a plurality of discrete locations on said body; and
   generating and presenting a video display showing the location, direction and magnitude of said dipole or said computed model values of said electrical activity characteristic in associating with a three dimensional representation of said body.

47. The display apparatus of claims 1, 21 or 25 wherein said at least one dipole is depicted as an obelisk-like image.

48. The display apparatus of claim 9, 16 or 19 wherein said dipole is depicted as an obelisk-like image.

49. An apparatus for displaying a topographic map of model values of brain electrical activity comprising:

means for receiving dipole data representing the location, direction and magnitude parameters that define at least one dipole;

means for computing from said dipole data model values of brain electrical activity for a plurality of locations;

means for generating interpolated model values of brain electrical activity from said computed model values; and means for displaying said computed and interpolated model values of brain electrical activity as a topographic map.

* * * * *